April 6, 1937. E. R. ASMUS, SR Plant Pat. 241
ROSE
Filed Nov. 4, 1936
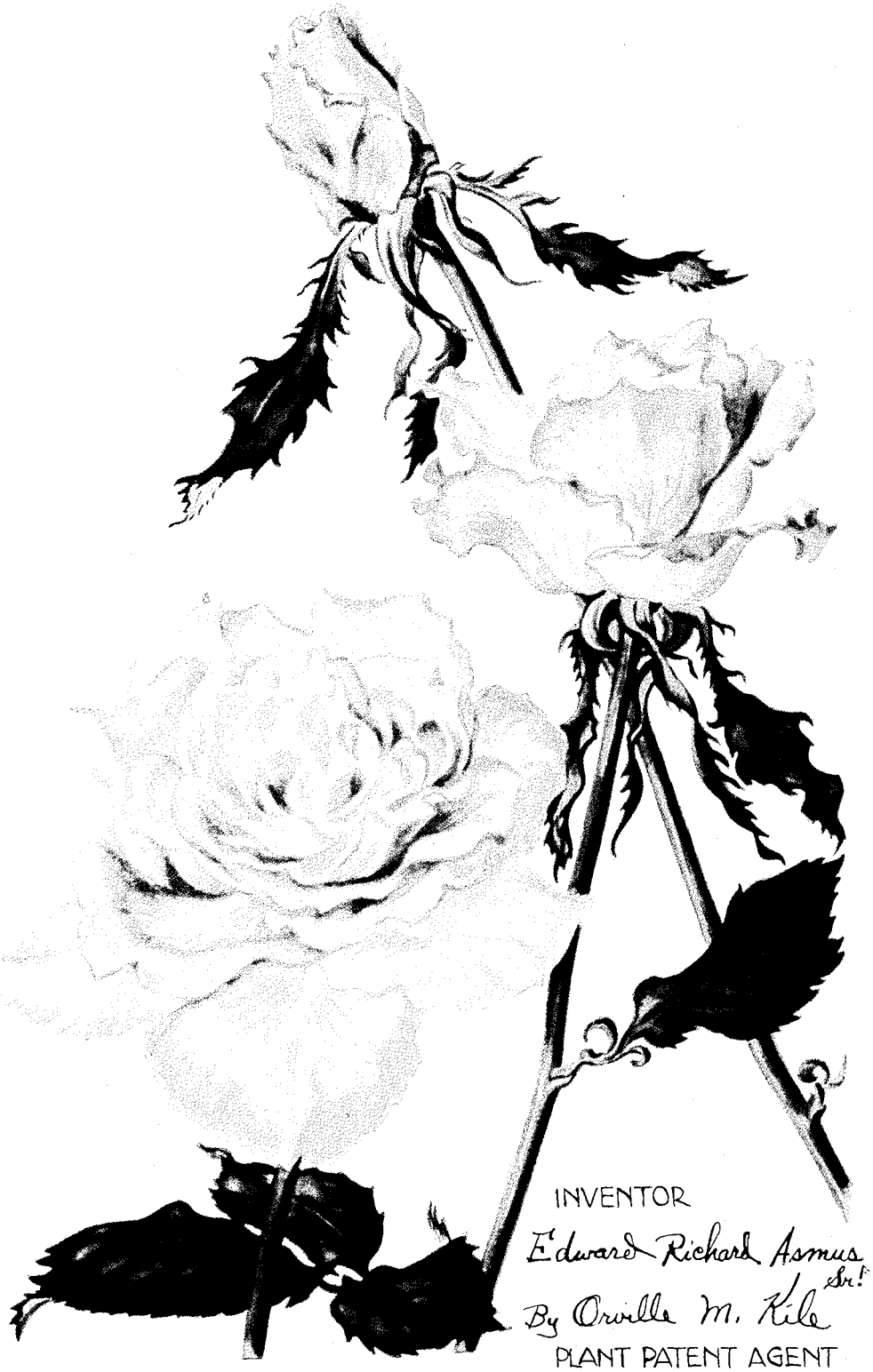
INVENTOR
Edward Richard Asmus Sr.
By Orville M. Kile
PLANT PATENT AGENT Patented Apr. 6, 1937

Plant Pat. 241

UNITED STATES PATENT OFFICE

241

ROSE

Edward Richard Asmus, Sr., Closter, N. J.

Application November 4, 1936, Serial No. 109,185

1 Claim. (Cl. 47—61)

My present invention relates to a new and distinct variety of rose plant of the hybrid tea class and it is a sport of Better Times. It was discovered in my gardens in October, 1934, and has been asexually reproduced, retaining its distinguishing characteristics in succeeding generations.

The accompanying illustrations show a bud, a half-opened flower and a full-blown flower of this variety, together with stems and foliage. Color references are to Ridgeway's Color Standards and Nomenclature.

Following is a more complete description of the plant and flower of this new variety:

*The plant*

*Growth.*—Vigorous and upright growth.

*Foliage.*—Moderately abundant.

*Leaves.*—Compound, usually five leaflets; usually the first leaf below the peduncle is a single leaflet and the next one consists of three leaflets.

*Leaflets.*—Oval; broad; sharply serrated; terminal leaflets average 2½ in. by 1¾ in. in size.

*Color.*—Upper surface is Elm Green (Plate XVII); lower surface is grayish green, some specimens having a reddish tinge on the under surface.

*Stems.*—Almost thornless; stiff; strong; Biscay Green (Plate XVII).

*Rachis.*—Medium width; upper side grooved and slightly hairy; under side smooth.

*Stipules.*—Long; cling to stem for some distance then end in two long sharp points—in some specimens these points curving backward.

*Sepals.*—Very foliaceous, two or three usually developing into deeply lanceolate serrated appendages about two inches long, and one of them often assuming the size and appearance of an elongated leaf.

*Disease resistance.*—Very resistant to diseases common to roses.

*Fragrance.*—Deliciously and lastingly fragrant.

*Keeping qualities.*—As a cut flower it is an usually good keeper.

*The flower*

Bud:

*Size.*—1½ to 2 inches long.

*Form.*—Slender and tapering, with a slightly crushed appearance at the base.

*Color.*—Almost a pure Rose Red (Plate XII), although not quite that dark. There is no color in Ridgway's just like it. The lower portion of the unopened bud has a velvety sheen and seems slightly darker than the terminal end.

Bloom:

*Size.*—Medium size, measuring 4 to 4½ inches across when fully open.

*Petalage.*—Double, having in October about 35 petals.

*Petals*—

*Substance.*—Thick and substantial.

*Surface.*—When the flower opens, the outer petals are dull inside and out. Inner petals are velvety on upper surface.

*Shape.*—The large outer petals are almost round but with somewhat crinkled and notched edges. Some have a slight point at the top which is emphasized by the crinkling. The smaller inner petals are long and much narrower. As the flower opens and grows older the petals recurve.

*Persistence.*—Petals cling until flower is dead, having recurved until the outer ones touch the stem.

*Veining.*—Prominent.

*Form.*—High-centered, opening out flat with slightly recurved petals, then finally folding backward.

*Color.*—The inside of the outer petals is rimmed with Rose Color (Plate XII) which diminishes to Deep Rose Pink (Plate XII) at the bottom of each petal. The outside of the outer petals is almost an even Rose Color (Plate XII) which deepens a little as the flower ages. The petals are darker progressively inward through Rose Red to Tyrian Rose (Plate XII). This latter color is brightened by the velvety surface of the upper side of the innermost petals. Some of the petals on some specimens have a vertical white stripe but this is not found on a large number of the petals. No yellow appears at the base of any of the petals.

*General color effect.*—The general color effect of the rose is not shown in Ridgway's but falls between Rose Color and Rose Red (Plate XII). When the bloom is several days old the petals recurve, showing the lighter portion at the base of each petal. In this way the general color effect is lightened as the flower ages, although there is no fading of the color. One of the remarkable and interesting features of this rose is its quality of retaining its brilliant Rose to Rose Red shade without fading until the flower withers.

*Reproductive organs*

*Stamens.*—Many; hidden until flower is fully opened.

*Filaments*—Red; medium length.

*Anthers.*—Large; yellow.

*Pollen.*—Scarce.

*Pistils.*—Many.

*Styles.*—Uneven; loosely bunched; white.

*Stigmas.*—Red with yellow tips.

*Ovaries.*—Partially protruding from calyx.

*Hips.*—Very small; tapering; same shade of green as peduncle (Biscay Green, Plate XVII); smooth.

*Comparison*

This new variety is more nearly like Premier Supreme than any other known variety. It differs from that variety, however, in the following respects: The color is much brighter than that of Premier Supreme and is non-fading. The plant is much more disease resistant than Premier Supreme, and is practically thornless whereas Premier Supreme has many thorns.

Another somewhat similar variety is Briarcliff Brilliance but this new variety differs particularly from Briarcliff Brilliance in the following respects: The color of this new variety is much more brilliant than that of Briarcliff Brilliance and is non-fading. There is no yellow at the base of the petals in the new variety while that is one of the features of Briarcliff Brilliance. The foilage is darker green, more abundant and broader than that of Briarcliff Brilliance. The shape of the blossom is somewhat different.

Having thus disclosed my invention, what I claim is:

A new variety of rose plant substantially as shown and described, characterized particularly by flowers of non-fading Rose to Tyrian Rose color as shown and described, its almost completely thornless peduncle and stems, and greater disease resistance as compared with Premier Supreme.

EDWARD RICHARD ASMUS, SR.